(12) United States Patent
Mendes

(10) Patent No.: US 10,775,372 B2
(45) Date of Patent: Sep. 15, 2020

(54) MOLECULAR SENSOR PREPARATIONS AND USES THEREOF

(71) Applicant: The University of Birmingham, Birmingham (GB)

(72) Inventor: Paula Mendes, Birmingham (GB)

(73) Assignee: THE UNIVERSITY OF BIRMINGHAM, Birmingham (GB)

( * ) Notice: Subject to any disclaimer, the term of this patent is extended or adjusted under 35 U.S.C. 154(b) by 31 days.

(21) Appl. No.: 15/116,501

(22) PCT Filed: Jan. 16, 2015

(86) PCT No.: PCT/GB2015/050086
§ 371 (c)(1),
(2) Date: Aug. 3, 2016

(87) PCT Pub. No.: WO2015/118294
PCT Pub. Date: Aug. 13, 2015

(65) Prior Publication Data
US 2017/0016893 A1  Jan. 19, 2017

(30) Foreign Application Priority Data

Feb. 4, 2014 (GB) .................................. 1401854.3

(51) Int. Cl.
| | | |
|---|---|---|
| *G01N 33/543* | (2006.01) | |
| *G01N 33/53* | (2006.01) | |
| *B01D 15/38* | (2006.01) | |
| *B01J 20/26* | (2006.01) | |
| *G01N 33/573* | (2006.01) | |

(52) U.S. Cl.
CPC ... *G01N 33/54386* (2013.01); *B01D 15/3852* (2013.01); *B01J 20/268* (2013.01); *G01N 33/5308* (2013.01); *G01N 33/573* (2013.01); *G01N 2333/922* (2013.01); *G01N 2333/96411* (2013.01); *G01N 2600/00* (2013.01); *G01N 2610/00* (2013.01)

(58) Field of Classification Search
CPC ............... B01D 15/3852; B01J 20/268; G01N 33/5308; G01N 33/54386; G01N 33/573; G01N 2600/00; G01N 2610/00; G01N 2333/922; G01N 2333/96411
See application file for complete search history.

(56) References Cited

U.S. PATENT DOCUMENTS

| 5,310,648 A | 5/1994 | Arnold et al. |
| 2003/0153001 A1 | 8/2003 | Soane et al. |
| 2012/0128536 A1 | 5/2012 | Jeong et al. |

FOREIGN PATENT DOCUMENTS

| WO | 97/33177 | 9/1997 |
| WO | 2004/016360 | 2/2004 |
| WO | 2007/023915 | 3/2007 |

OTHER PUBLICATIONS

Prasad et al. Enantioselective quantitative separation of D- and L-thyroxine by molecularly imprinted micro-solid phase extraction silver fiber coupled with complementary molecularly imprinted polymer-sensor. J. Chromatography A, 2010, pp. 4255-4266. (Year: 2010).*
Gao et al. Smart surface imprinting polymer nanospheres for selective recognition and separation of glycoprotein. Colloids and surfaces A: Physicochem. Eng. Aspects 2013, vol. 433, pp. 191-199. (Year: 2013).*
Lin et al. Preparation of boronate-functionalized molecularly imprinted monolithic column with polydopamine coating for glycoprotein recognition and enrichment. J. Chromatography A 2013, vol. 1319, pp. 141-147. (Year: 2013).*
Li et al. Photolithographic boronate affinity molecular imprinting: A general and facile approach for glycoprotein imprinting. Agnew. CHem. Int. Ed. 2013, vol. 52, pp. 7451-7454. (Year: 2013).*
EPO Communication dated Jan. 10, 2018, Application No. 157018318.
Li, L. et al. Wiley-Vch 2013 et al: "Supporting Information Photolithographic Boronate Affinity Molecular Imprinting: A General and Facile Approach for Glycoprotein Imprinting", Jun. 13, 2013 (Jun. 13, 2013), XP055437341.
United Kingdom Search Report dated Oct. 15, 2014, Application GB1401854.3.
Berube, M., et al., "Benzoboroxoles as Efficient Glycopyranoside-Binding Agents in Physiological Conditions: Structure and Selectivity of Complex Formation", J. Org. Chem., 2008, pp. 6471-6479, vol. 73.

* cited by examiner

*Primary Examiner* — Shafiqul Haq
(74) *Attorney, Agent, or Firm* — Gates & Cooper LLP

(57) ABSTRACT

The present invention relates to a method of preparing a molecular sensor that is specific for a target molecule having a saccharide or peptide region. The method comprises using the target molecule as a template and incubating the template with a receptor to form a template-receptor complex. A molecular scaffold is formed on a surface around the template-receptor complex such that the receptor and at least a portion of the template are embedded in the scaffold, and the template is removed to produce a cavity defined by the scaffold, such that the cavity is complementary to at least a portion of the saccharide or peptide region of the target molecule.

21 Claims, 5 Drawing Sheets

Panel A

Panel B

MOLECULAR SENSOR PREPARATIONS AND USES THEREOF

The present invention relates to methods of preparing molecular sensors, in particular methods of preparing molecular sensors which are specific for a target molecule, the molecular sensors produced thereby and uses of the molecular sensors.

Glycosylation, the addition of carbohydrate structures to protein backbones, is known to affect the function and half-life of a number of proteins. Altered glycosylation has been associated with many human diseases such as cancer, immune deficiencies, neurodegenerative diseases, hereditary disorders and cardiovascular diseases. In fact, many clinical biomarkers in cancer are glycoproteins and, since glycoproteomics is rapidly emerging as an important technique for biomarker discovery, glycoproteins are expected to become increasingly important to the diagnosis and management of human diseases. Antibodies are currently widely used as receptor sites in the detection, quantification and purification of many proteins including clinically relevant glycoproteins. However, the production of antibodies is an expensive and time consuming exercise. Furthermore, the peculiarities of intracellular machinery, which is utilized in the commercial production of antibodies, is not ideally suited for the production of high affinity antibodies against carbohydrate-based antigens. A further limitation is that, as antibodies themselves are proteins, they are susceptible to degradation by conditions of high temperature, moderate change in pH and UV light. For all of these reasons, a more robust synthetic alternative would be highly sought after.

Molecular imprinting is a template directed process, where polymer networks are formed around compounds of interest, literally producing a molecular mould of these molecules. The template molecules are removed, leaving behind a complementary binding site for the target molecule, much akin to the binding site of antibodies. In this way artificial binding sites may be produced and used in a number of settings, including chromatographic separation, sensors, catalysis and drug delivery. However, while this technology has been successfully developed for small molecules, intrinsic limitations in the scalability of traditional molecular imprinting techniques has been hindering the imprinting of large molecules such as proteins with the desired affinity and selectivity. Specifically, key issues include protein entrapment, poor re-binding kinetics and heterogeneity in binding pocket affinity.

The present invention has been devised with these issues in mind.

According to a first aspect of the present invention there is provided a method of preparing a molecular sensor that is specific for a target molecule having a saccharide or peptide region, the method comprising:

using the target molecule as a template, incubating the template with a receptor to form a template-receptor complex;

forming a molecular scaffold on a surface around the template-receptor complex such that the receptor and at least a portion of the template are embedded in the scaffold; and removing the template to produce a cavity defined by the scaffold, wherein the cavity is complementary to at least a portion of the saccharide or peptide region of the target molecule.

According to a second aspect of the present invention there is provided a molecular sensor that is specific for a target molecule and is obtainable by the method of the first aspect of the present invention.

According to a third aspect of the invention there is provided a molecular sensor that is specific for a target molecule having a saccharide or peptide region, the molecular sensor comprising a molecular scaffold immobilized on a surface, wherein the molecular scaffold defines a cavity which is complementary to at least a portion of the target molecule, the cavity comprising a receptor for the saccharide or peptide region of the target molecule at a surface thereof.

By "specific for", it will be understood that the molecular sensor binds preferentially to the target molecule. The sensor may bind a number of different molecules to some extent, but the binding thermodynamics and kinetics may favour the binding of the target molecule.

According to a fourth aspect of the present invention there is provided a method of detecting, quantifying and/or purifying a target molecule using a molecular sensor in accordance with the second or third aspect of the invention.

The present invention provides a synthetic recognition platform based on molecular imprinting concepts that exhibits antibody-like behavior and exceptionally high selectively for target molecules having saccharide or peptide regions. The molecular sensors of the invention provide a synthetic alternative to antibodies (where the target molecule is a protein), and may be used in the binding, detection, quantification and/or purification of target proteins. The molecular sensors may therefore be considered as antibody mimics in that they are highly specific for their target protein. However, the synthetic sensors of the invention are advantageous in that they are more stable and more resistant to changes in pH, temperature and UV light than antibodies.

The cavity defined by the molecular scaffold provides a recognition site for receiving a part or a whole of the target molecule. The cavity is complementary to at least a portion of the target molecule. By "complementary to" it will be understood that the size and shape of the cavity, and the recognition sites of receptors within the cavity, are tailored to the target molecule, or a portion thereof.

The stepwise construction of the molecular sensor enables a greater degree of control over the shape, size and recognition sites of the resulting cavity than could be achieved by previous molecular imprinting techniques. As a result, greater selectivity is achieved and problems such as non-specific binding and entrapment of the template are mitigated.

The following statements may apply to the first, second, third or fourth aspects of the invention, as appropriate.

The target molecule may be any molecule that contains a monosaccharide or amino acid residue. Examples include proteins, polypeptides, glycosylated proteins, glycated proteins, saccharides (mono-, di- and oligosaccharides) and nucleosides.

In some embodiments, the target molecule is a protein, for example a glycoprotein. Many clinical biomarkers of cancer are glycoproteins, and glycoproteins are expected to become increasingly important to the diagnosis and management of human diseases. Examples of glycoproteins include, but are not limited to, CEA in colorectal cancer, CA125 in ovarian cancer, HER2 in breast cancer, PSA in prostate cancer and α-fetoprotein in liver cancer.

In other embodiments, the target molecule is an oligosaccharide (including disaccharides) such as those present in the glycoprotein biomarkers mentioned above.

The purpose of the receptor is to selectively and reversibly bind the target molecule. During formation of the molecular scaffold, the receptor tethers the target molecule, which functions as a template. The receptor becomes embedded in the scaffold. When the template is removed, the receptor may be left behind such that it comprises a part of the resulting cavity. By this, it will be appreciated that the receptor may form a part of the surface of the resulting cavity, or that it may project into the cavity. During subsequent use of the sensor, the receptor interacts with target molecules which are received within the cavity. In this way, the receptor also contributes to the specificity of the sensor.

The molecular sensor of the invention need not be limited to the detection of a single target molecule, but may be capable of binding two or more target molecules. A molecular sensor capable of detecting two or more different target molecules may be prepared by simultaneously imprinting two or more different templates. The advantage of multiple template imprinting is that several different classes of molecules can be detected at one time. For example, a method of preparing a molecular sensor that is specific for a first and a second target molecule may comprise:

using the first target molecule as a first template and the second target molecule as a second template, incubating the first template with a first receptor to form a first template-receptor complex, and incubating the second template with a second receptor to form a second template-receptor complex;

forming a molecular scaffold on a surface around the first and second template-receptor complexes such that the first and second receptors and at least a portion of the first and second templates are embedded in the scaffold; and removing the first and second templates to produce first and second cavities defined by the scaffold, wherein the first cavity is complementary to at least a portion of the first target molecule and the second cavity is complementary to at least a portion of the second target molecule.

In some embodiments the receptor comprises a recognition motif which binds preferentially to the target molecule. In some embodiments, the recognition motif binds only to the target molecule, and not to any other molecules. The recognition motif may be chosen to interact with specific residues, functional groups, or structural or sequence motifs of the target molecule. In embodiments wherein the target molecule is a glycoprotein, the recognition motif may be capable of interacting with the saccharide and/or the protein parts of the glycoprotein.

It will be appreciated that "a receptor" refers to one or more receptor molecules.

One or more recognition motifs may be incorporated into the receptor to enable interaction with the target molecule. For example, a recognition motif may provide π-surfaces, hydrogen-bonding domains and/or polar residues, all of which are known to be involved in biological saccharide recognition and protein interactions. Further examples include aromatic and/or conjugated functional groups which may be incorporated for CH-π and hydrophobic interactions respectively, while acid and/or phosphate groups may be incorporated to provide polar interactions.

In some embodiments, the recognition motif comprises, or is constituted by, a boronic acid (BA) group. Boronic acids reversibly bind carbohydrates, nucleosides and other cis-diols to form five- or six-membered cyclic boronic acid esters in aqueous alkaline solution. The cyclic esters dissociate when the medium is changed to acidic pH. This chemistry makes BA groups ideal candidates as recognition moieties in glycoprotein receptors.

In some embodiments, the receptor comprises an amino acid or a peptide. In particular embodiments, the receptor comprises a hydrophobic amino acid (e.g. phenylalanine, tryptophan, valine, tyrosine) or a polar amino acid (e.g. aspartic acid, glutamic acid). The amino acid or peptide, or a part thereof, may constitute the recognition motif of the receptor. The peptide sequence may be specific for the target protein.

In some embodiments, the receptor comprises a nucleotide or nucleic acid.

In some embodiments, the receptor further comprises a first binding moiety for binding the template-receptor complex to the molecular scaffold. The first binding moiety may be capable of reacting with one or more of the molecules which form the molecular scaffold so as to form a covalent bond between the receptor and the scaffold molecules. In some embodiments, the first binding moiety is a polymerizable group. Examples of suitable polymerizable groups include acrylamide and vinyl groups. Optionally, the first binding moiety is joined to the recognition motif by a linker, such as an alkyl or aryl linker.

Examples of receptors include (4-acrylamidophenyl)boronic acid (AM-BA), N-isopropylacrylamide, acrylamide, N,N'-methylenebisacrylamide, acrylamide functionalized amino acids (e.g. acrylamide functionalized phenylalanine, asparagine or tryptophan) and 2-acrylamidoethyl dihydrogen phosphate. However, it will be appreciated that the receptor will be selected according to the nature of the target molecule.

The selection and combination of recognition moieties enables the preparation of receptors, and thus the resulting binding cavities, that are selective not only for specific proteins but also for individual isoforms of the same protein.

The template-receptor complex may be formed by mixing a solution of the receptor molecules with a solution of the target molecule. The ratio of receptor: target molecule molecules in the mixture may be from 1:1 to 1:20 or from 1:5 to 1:15, such as 1:10. Isothermal titration calorimetry (ITC) may be used to determine the receptor: target molecule molar ratio required for saturation binding. It is preferred to avoid an excess of receptor molecules which could interfere with the imprinting quality and binding characteristics of the resulting cavity. The mixture may be incubated for a period of time sufficient to enable most or substantially all of the receptor molecules to bind to a target molecule molecule. The mixture may be incubated for a period of time of from 1 minute to 2 hours, or from 30 to 60 minutes.

The resulting template-receptor complex may comprise a single template bound to a single receptor, or it may comprise a single template bound to more than one receptor. In some embodiments, the template-receptor complex comprises at least 2, at least 3, or at least 4 receptors bound to a single template.

In some embodiments, the surface is a planar surface.

The surface may be a metal surface, such as gold or silver. Alternatively, the surface may be a non-metal, such as silicon, silicon dioxide, silicon carbide, silicon nitride, aluminium oxide or glass. In particular embodiments, the surface is gold.

In other embodiments, the surface is curved. In particular, the recognition site may be formed on the surface of a nanoparticle. The nanoparticles may have a metal (e.g. Au or Ag) or non-metal (e.g. silicon dioxide) surface It will be appreciated that a "molecular scaffold" is a structure formed from a network of molecules. By forming the network around the template-receptor complex, the scaffold is moulded to the shape of at least a part of the molecule template. The molecular scaffold is stable such that on removal of the template an impression (i.e. a cavity) is left in the scaffold in the shape of that part of the template.

The molecular scaffold may be formed from a first type of molecules (also referred to herein as "first molecules"). In some embodiments, each of the first molecules comprises a tether moiety which tethers the molecular scaffold to the surface. The tether moiety is typically a functional group which has a strong affinity to the surface and anchors the first molecules to it. Examples of tether moieties include thiols (capable of binding to, for example, gold, silver and copper), organosilanes (capable of binding to hydroxylated surface (e.g. $SiO_2$ for binding to silicon surfaces; $Al_2O_3$ for binding to aluminium and glass surfaces), dialkyl sulfides (capable of binding to gold), alcohols or amines (capable of binding to platinum) and carboxylic acids (capable of binding to aluminium oxide, silver and indium tin oxide). In some embodiments, the tether moiety is a sulfur group, such as a thiol or disulfide group.

In some embodiments, the step of forming the molecular scaffold comprises exposing the surface to the first type of molecules. The first type of molecules may be adsorbed onto the surface, by virtue of their tether moieties, to form an assembly. The assembly may be considered a self-assembled monolayer (SAM). Thus, in some embodiments, the step of forming the molecular scaffold comprises forming a SAM.

It will be appreciated by those skilled in the art that a SAM is an organized molecular assembly which is formed spontaneously by adsorption of molecules to a surface. The molecules which form the SAM may be referred to as 'SAM molecules'. In some embodiments, the first type of molecules may be considered SAM molecules.

A self-assembled monolayer may be formed by depositing SAM molecules onto the surface, e.g. by physical vapor deposition techniques, electrodeposition or electroless deposition. Such techniques will be known to those skilled in the art. Alternatively, a SAM may be formed by immersing the surface in a solution of SAM molecules. The surface will be immersed for a period of time that is sufficient for the SAM molecules to be adsorbed onto the surface. The surface may be immersed for a period of time of from 30 minutes to 30 hours. In some embodiments, the surface is immersed for at least 1 hour, at least 5 hours, at least 10 hours or at least 15 hours. In some embodiments, the surface is immersed at a temperature of from 5 to 50° C., from 10 to 40° C. or from 18 to 30° C. In further embodiments, the surface is immersed at approximately room temperature.

In some embodiments, the method comprises exposing the surface to the first type of molecules in the presence of the template-receptor complex. This may result in simultaneous adsorption of the first type of molecules and the complex onto the surface. Thus, in some embodiments the method of forming the molecular scaffold comprises forming a SAM on the surface in the presence of the template-receptor complex.

The method may further comprise cross-linking the first type of molecules of the scaffold. As will be known to those skilled in the art, cross-linking comprises forming covalent bonds between adjacent molecules so at to provide a rigid network. The cross-links may be formed directly between adjacent molecules (e.g. by reaction between functional groups on adjacent molecules), or they may be formed indirectly between molecules (e.g. via a further cross-linking molecule).

Thus, the molecular scaffold formed on the surface may be a cross-linked film. The term "film", as used herein, will be understood to mean a layer or a multilayer of molecules. Typically, a film may have a thickness of from 1 to 10 nm, or from 2 to 5 nm. By "cross-linked", it will be understood that some or all of the molecules of the film are joined to one or more other molecules of the film, typically by covalent bonds, thereby forming a network.

In some embodiments, each of the first type of molecules additionally comprises a second binding moiety (i.e. in addition to the tether moiety) which is capable of binding to (e.g. forming covalent bonds with) other first molecules, the receptor, and/or further molecules. In some embodiments, the second binding moiety is a polymerizable group, such as a vinyl or acrylamide group. In other embodiments, the second binding moiety is a functional group capable of initiating polymerization. Forming the molecular scaffold may therefore comprise initiating polymerization between the polymerizable groups present on the first molecules, the receptors and/or further molecules.

In some embodiments, the method of preparing a molecular sensor comprises:
  using the target molecule as a template, incubating the template with a receptor to form a template-receptor complex, wherein the receptor comprises a polymerizable group;
  exposing a surface to a first type of molecules in the presence of the template-receptor complex, each of the first type of molecules comprising a tether moiety and a polymerizable group;
  initiating polymerization between the polymerizable groups so as to form a molecular scaffold on the surface around the template-receptor complex, wherein the receptor is covalently bound to the scaffold and at least a portion of the template is embedded in the scaffold; and
  removing the template to produce a cavity defined by the scaffold, wherein the cavity is complementary to at least a portion of the saccharide or peptide region of the target molecule.

Polymerization may be initiated using an initiator such as ammonium persulfate (APS).

In some embodiments, the method comprises forming a SAM on the surface in the absence of the template-receptor complex.

In some embodiments, the molecular scaffold is formed from a first type of molecules and a second type of molecules (also referred to herein as "second molecules"). It will be understood that the length of the first and/or second molecules will be chosen according to the dimensions of the target molecule. It may be desirable to enclose a significant portion of the surface of the molecule within the scaffold in order to maximize the specificity of the resulting cavity. In some embodiments, at least one of the first and second molecules comprises an elongate moiety, which provides structure to the molecular scaffold around the template-receptor complex. By "elongate", it will be understood that the moiety comprises a linear chain of at least 4, at least 6, at least 8, or at least 10 atoms. In some embodiments, the elongate moiety is an oligomer. As will be appreciated by those skilled in the art, an "oligomer" is a chemical chain consisting of a few repeat units, e.g. from 2 to 20 or from 3 to 10 repeat units. Suitable oligomers include hydrocarbon chains and oligomers of ethylene glycol i.e. oligo(ethyleneglycol) (OEG)).

The elongate moiety may be inert, in that it is substantially non-reactive with the template. The elongate moiety may be an oligomer of substantially non-reactive groups.

In some embodiments, each of the first molecules further comprises a first coupling moiety for coupling to the second molecules.

In some embodiments, each of the second molecules comprises a second coupling moiety, for coupling to the first molecules, to other second molecules and/or to the receptors. In some embodiments, the second molecules comprise two or more second coupling moieties. In further embodiments, the second coupling moiety is a polymerizable group, such as a vinyl or acrylamide group. In some particular embodiments, the second molecules are capable of forming cross-links between the first molecules within the molecular scaffold. In these embodiments the second molecules may be considered to be cross-linking molecules.

In some embodiments, the method of preparing the molecular sensor comprises:
    forming a SAM on a surface from a first type of molecules;
    using the target molecule as a template, incubating the template with a receptor to form a template-receptor complex, and binding the template-receptor complex to the SAM;
    immobilizing a second type of molecules on the SAM so as to form a molecular scaffold around the bound template; and
    removing the template to produce a cavity defined by the molecular scaffold, wherein the cavity is complementary to at least a portion of the saccharide or peptide region of the target molecule.

In some embodiments, each first type of molecule ("first molecule") comprises a tether moiety for tethering the SAM to the surface, a second binding moiety for binding to the receptor, and a first coupling moiety for coupling to the second type of molecules.

In some embodiments, each second type of molecule ("second molecule") comprises a second coupling moiety for coupling to the first molecules.

In some embodiments, the second molecules are immobilized on the SAM by a reaction between the first coupling moieties of the first molecules ("SAM molecules") and the second coupling moieties of the second molecules.

The first and second coupling moieties may be any chemical groups which are capable of interacting so as to couple the first and second molecules together. In some embodiments, the first and second coupling moieties may be capable of reacting to form a covalent bond between the first and second molecules. For example, the first and second coupling moieties may be acrylamide groups which are capable of polymerizing to immobilize the second molecules on the SAM formed by the first molecules. Other suitable pairs of chemical groups which may constitute the first and second coupling moieties include maleimide and thiol groups, which are capable of reacting to form a stable thioether bond, and aminooxy and aldehyde or ketone groups, which react under mild aqueous conditions to form an oxime bond. It will be appreciated that other suitable chemical groups will be known to the skilled person.

In further embodiments, the second molecules are immobilized on the SAM by a click reaction between the first coupling moieties of the first molecules and the second coupling moieties of the second molecules. In particular embodiments, the first coupling moiety is one of an alkyne or an azide group, and the second coupling moiety is the other of an alkyne or an azide group. Click chemistry is advantageous since it allows the reaction to be carried out with high selectivity and yield under extremely mild conditions.

In some embodiments, each first molecule comprises a thiol or disulfide tether moiety, a polymerizable binding moiety (e.g. acrylamide) and an alkyne or azide first cross coupling moiety. In some particular embodiments, the first molecule is (N,N'-(disulfanediylbis(1-oxo-1-(prop-2-yn-1-ylamino)propane-3,2-diyl))diacrylamide (AAM-SS).

In some embodiments, each of the second molecules comprises an elongate moiety derived from a peptide (e.g. an oligopeptide), a hydrocarbon chain (e.g. a hydrocarbon oligomer), or ethylene glycol (e.g. an ethylene glycol oligomer (OEG)).

In some embodiments, each of the second molecules comprises an OEG moiety. An OEG moiety is conveniently flexible and facilitates the accommodation of the non-rigid structure of the molecules bound to the layer of first molecules. OEG backbones help to prevent non-specific molecule interaction, as well as providing hydrogen bonding sites within the formed surface cavities.

It will be appreciated that the number of repeats of an oligomer forming the second molecules will depend on the dimensions of the molecule. For example, the number of ethylene glycol units in a backbone may be from 2-20, or from 3-10 (e.g. from 3 to 5 or from 6 to 10). Alternatively, each second molecule may comprise a single ethylene glycol unit.

In some embodiments, the second molecule is O-(2-azidoethyl)heptaethylene glycol.

The step of binding the template-receptor complex to the SAM may comprise mixing the SAM-functionalized surfaces with the template-receptor complexes in solution. The mixture may be incubated for a period of time sufficient to enable most or substantially all of the second binding moieties of the first molecules to bind to a template-receptor complex. The mixture may be incubated for a period of time of from 1 minute to 1 hour. In embodiments wherein the first and second binding moieties are polymerizable groups, the template-receptor complex is bound to the SAM by cross-linking the polymerizable groups. Cross-linking may be initiated by adding an oxidizing agent, such as ammonium persulfate (APS).

The step of immobilizing the second molecules on the SAM may comprise adding the second molecules (e.g. in solution) to the template-receptor complexes bound to the SAM-functionalized surfaces. Depending on the nature of coupling groups, the second molecules may spontaneously couple to the SAM by reaction between the first coupling groups on the first molecules and the second coupling groups on the second molecules. However, in some instances, the method further requires the addition of a catalyst. For example, in embodiments wherein the second molecules bind to the SAM via click chemistry, a copper sulphate catalyst and sodium ascorbate reducing agent may be used. The mixture may be allowed to react for a period of from 30 minutes to 6 hours.

In some alterative embodiments, the molecular scaffold is formed by controlled radical polymerization (CRP) techniques, such as atom transfer radical polymerization (ATRP) or reversible addition-fragmentation chain transfer (RAFT). ATRP is a method by which carbon-carbon bonds can be formed using a catalyst. These techniques have been shown to form uniform films with well-controlled thickness. In particular, ATRP is able to form well-controlled cross-linked films under ambient conditions and using water-containing solutions, making it particularly convenient for use with proteins and oligosaccharides.

CRP-based techniques also require formation of a SAM on the surface. However, in CRP-based methods, the template-receptor complex is bound to the SAM simultaneously with formation of the molecular scaffold.

Thus, in some embodiments, the method of preparing the molecular sensor comprises:

forming a SAM on a surface using first molecules;
using the target molecule as a template, incubating the template with a receptor to form a template-receptor complex;
exposing the SAM-functionalized surface to a mixture of second molecules, the template-receptor complex and a catalyst so as to effect ATRP between the first molecules, the second molecules and the receptor, thereby forming a molecular scaffold around the template; and
removing the bound template to produce a cavity defined by the molecular scaffold, wherein the cavity is complementary to at least a portion of the saccharide or peptide region of the target molecule.

In some embodiments the receptor comprises a recognition moiety and a polymerizable group An ATRP initiator is required for polymerization to occur. In some embodiments, each of the first molecules (i.e. the SAM molecules) comprises an ATRP initiator. The ATRP initiator may constitute the second binding moiety of the first molecules. The ATRP initiator may be an alkyl halide, for example a tertiary bromide group.

In further embodiments, each first molecule comprises a tether moiety for anchoring the SAM to the surface, and an ATRP initiator. The tether moiety and the ATRP initiator may be joined by a linker, such as an alkyl chain. In some embodiments, the first molecule is 11-mercaptoundecyl 2-bromo-2-methylpropanoate.

CRP results in the formation of a molecular scaffold by cross-linking the second molecules, the first (SAM) molecules and the receptors. Thus, in some embodiments, the second cross-coupling moiety of each second molecule is a polymerizable group, such as a vinyl group. In further embodiments, each of the second molecules comprises at least two polymerizable groups. The second molecules may be terminated at each end with polymerizable groups. Suitable scaffold monomers include ethylene glycol dimethacrylate, propylene glycol dimethacrylate, 1,4-butanediol dimethacrylate, 1,6-hexandiol dimethacrylate, trimethylolpropane dimethacrylate, 1,2-ethandiol divinyl ether, divinyl benzene and divinyl ether, although other suitable molecules will be apparent to the skilled person.

In the resulting molecular scaffold, the second molecules form cross-links between the first molecules, thereby providing a network. The receptors may be bound to the scaffold via the second molecules, rather than by direct covalent bonding with the first molecules.

Exposing the SAM-functionalised surface to a mixture of second molecules, the complex and the catalyst may comprise immersing the SAM-functionalized surface in an aqueous solution containing the second molecules, the complex and the catalyst. The SAM-functionalized surface will be immersed for a period of time sufficient for polymerization to occur to produce a molecular scaffold of the desired thickness. It will be appreciated that the desired thickness of the molecular scaffold will depend on the dimensions of the target molecule. For example, the desired thickness may be from 1 to 3 nm, or from 1.5-2 nm, but it may be more or less depending on the molecule of interest. A period of time sufficient for polymerization to occur may be from 5 minutes to 12 hours, from 10 minutes to 6 hours or from 15 minutes to 3 hours (e.g. 30 minutes).

In some embodiments, polymerization may be effected by providing a first solution containing the SAM-functionalized surface, providing a second solution containing the catalyst, the second molecules and the complex (and optionally a ligand), and gradually combining the first and second solutions. The first and second solutions may be combined over a period of time of from 10 minutes to 12 hours. The polymerization reaction may be carried out under an inert atmosphere (e.g. nitrogen). The method may be carried out as described by Ma et al. (Advanced Materials, 2004, 16, No. 4, pages 338-341).

The catalyst may be $CuCl$, $CuBr_2$, $FeCl_3.6H_2O$, $FeBr_3$, or a combination thereof.

The reaction mixture may further comprise a ligand. The primary role of a ligand in an ATRP catalyst complex is to solubilize the transition metal salts in the polymerization medium and to adjust the redox potential of the metal center to provide an appropriate activity and dynamics for the repetitive halogen exchange reaction. Suitable ligands include 2,2'-bipyridine, diethylenetriamine (DETA), triethylenetetramine (TETA) and N,N,N',N'',N''-pentamethyldiethylenetriamine.

In the final step of preparing the molecular sensor, the template is removed, leaving behind a cavity (i.e. a binding site) that is complementary to, and specific for, the target molecule. Since the molecule template is reversibly bound to the receptor, the template can be easily released without causing damage to the scaffold. The molecule template may be removed by washing with a solvent. It will be appreciated that the type of solvent required to dissociate the template from the receptor will be selected according to the nature of the interaction between the molecule and the receptor, which in turn will depend on the functional groups present in the receptor. In some embodiments, the template can be released by washing with water or a suitable buffer such as an acidic aqueous solution, a borate buffer or an elution buffer containing Tris or sorbitol. Other suitable solutions will be apparent to the skilled person. It will be appreciated that the type of washing solution may depend on the nature of the interaction of the interaction between the target molecule and the receptor.

It will be appreciated that the size and shape of the resulting cavity of the sensor will be determined by factors including the nature of the target molecule (template) and the length of the first and second molecules.

It is envisioned that the synthetic molecule recognition technology of the present invention could be used in combination with a wide range of biosensors, including electrochemical, acoustical, and optical sensors.

The molecular sensor of the invention may be used in a method for detecting, quantifying and/or purifying a target molecule. The method may comprise exposing the molecular sensor, or a plurality of molecular sensors, to a sample of fluid containing (or thought to contain) the target molecule, thereby allowing target molecules (if present) to be received within the cavities of the molecular sensors.

A method of detecting a target molecule in a sample of fluid may further comprise detecting the presence of the bound target molecule within the cavity of the sensor. The target molecule may be detected by electrochemical (such as those employing amperometric and potentiometric detectors), acoustical (e.g. quartz crystal microbalances) or optical (e.g. surface plasmon resonance (SPR)) methods. SPR is advantageous in that it has high sensitivity and speed of response, low target consumption, enables real-time detection of interactions and is capable of working with complex body fluids such as urine and serum.

For example, detection and quantification may be performed using an optical sensor such as surface plasmon resonance (SPR). A small sample volume (e.g. 10 μl to 200 μl) may be injected over the molecular sensor over a period of time that may range from 5 min to 30 min. A flow delivery system may be incorporated into the SPR to assure the injection of precise volumes. After quantification of the detection of the target molecule by the sensor, signal intensities may either be converted to mass units using calibration curves or evaluated qualitatively.

A method of purifying a target molecule may further comprise releasing the target molecules from the cavities. The target molecules may be released by washing with a solvent, for example water, an acidic aqueous solution or an elution buffer containing Tris or sorbitol.

A method of quantifying a target molecule may comprise quantifying the molecule while it is captured by the sensor. Alternatively, the molecule may be released from the cavities of the molecular sensor prior to quantification.

The fluid may comprise a mixture of molecules. In some embodiments, the fluid is a biological fluid, such as blood, plasma or urine, or another complex biological medium such as cell culture medium. Since the molecular sensors of the invention are highly specific for the target molecule, they are able to selectively bind the molecule of interest from a complex mixture of molecules.

The presence or quantity of certain proteins or glycoproteins in biological fluids may be indicative of disease. Altered glycosylation is associated with diseases and conditions such as cancer, immune deficiencies such as rheumatoid arthritis, systemic lupus erythematosus and HIV-associated autoimmune phenomena, neurodegenerative diseases, hereditary disorders such as hereditary multiple exostoses, and cardiovascular diseases. The molecular sensors described herein may conveniently be able to distinguish between different isoforms of the same protein, and thus may be capable of detecting altered glycosylation of proteins. The methods and sensors of the invention may therefore find use in diagnostic methods for the detection and/or monitoring of such diseases. However, it will be appreciated that the methods and sensors of the invention may also find use in monitoring the presence and/or levels of target proteins in healthy populations.

Thus, the present invention also resides in a method for diagnosing or monitoring the treatment of a disease or condition comprising detecting the presence of and/or quantifying the amount of a target molecule in a fluid sample using the molecular sensor of the present invention. the presence or concentration of the target molecule may be indicative of a particular condition or disease of a human or animal subject. For example, the target molecule may be a biomarker for the disease or condition.

The fluid sample may have been obtained from a human or animal subject known to have, or suspected of having, the disease or condition. It will be understood that the sample was previously obtained from the human or animal, such that the sampling itself does not form part of the method of the invention.

The disease or condition may be selected from the group consisting of cancer, immune deficiencies (for example rheumatoid arthritis, systemic lupus erythematosus and HIV-associated autoimmune phenomena), neurodegenerative diseases, hereditary disorders such as hereditary multiple exostoses, and cardiovascular diseases.

The first and second molecules and receptors will be synthesized following standard organic methodologies known to those skilled in the art.

The present invention further resides in a device for diagnosing or monitoring the treatment of a disease or condition, the device comprising a molecular sensor in accordance with the second or third aspect of the invention. Such a device may be adapted to provide bench-top testing of patient samples. Alternatively, the device may be adapted to be used as a self-monitoring and diagnosis system. Conveniently, the device may be hand-held.

Embodiments of the invention will now be described by way of example and with reference to the accompanying Figures, in which.

Figure 4:
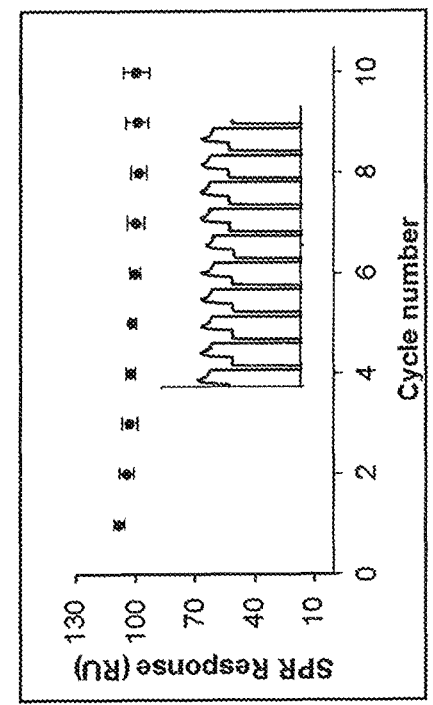
Figure 6:
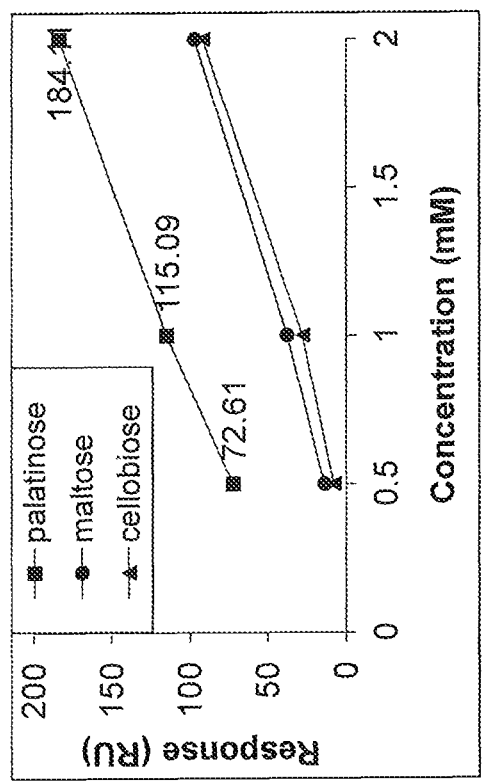
Figure 6:
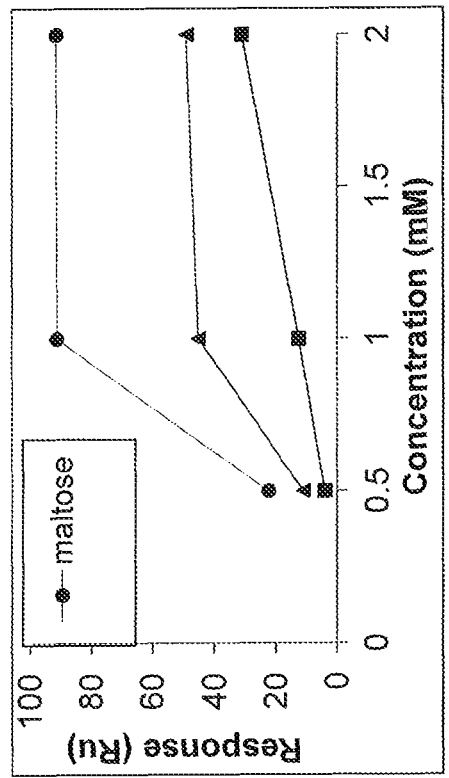

FIG. 4 is a plot of the surface plasmon resonance signals, in response units (RU), representing protein binding to a molecular sensor prepared using RNase B as a template over a number of cycles; and FIG. 6 is a plot of the surface plasmon resonance signals, in response units (RU), representing disaccharide binding to a non-inventive BA-terminated surface (panel A) and a molecular sensor prepared using maltose as a template (Panel B).

Figure 5:
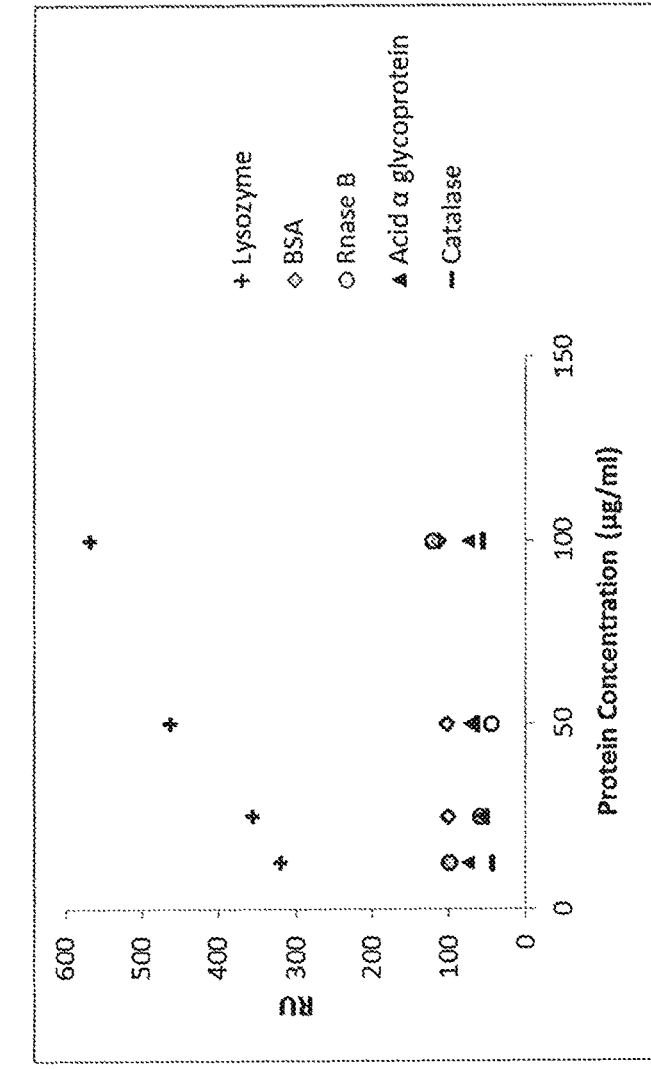

FIG. 5 is a plot of the surface plasmon resonance signals, in response units (RU), representing protein binding to a molecular sensor prepared using lysozyme as a template.

Figure 1:
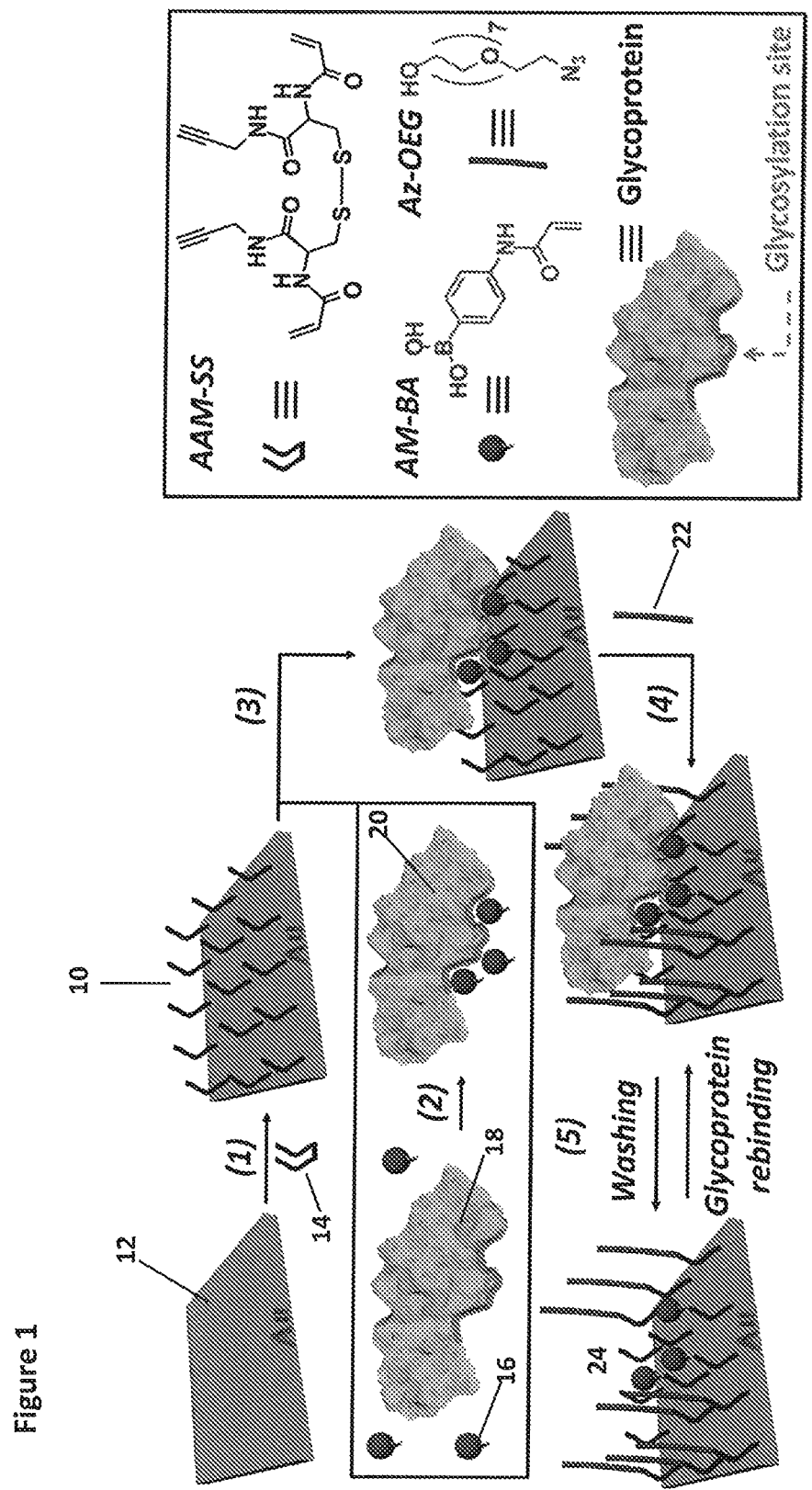
FIG. 1 is a schematic diagram showing the steps in the formation of a molecular sensor for a target protein according to an embodiment of the present invention.

With reference to FIG. 1, a molecular sensor specific for a target molecule may be built in a stepwise manner from molecular building blocks using both self-assembly and molecular imprinting techniques. In step (1) a self-assembled monolayer (10) is formed on a gold surface (12) from molecules of AAM-SS (14). Each AAM-SS molecule provides two SAM molecules, each comprising a disulfide tether moiety for binding to the gold surface (12), an acrylamide polymerizable group for binding to the template-receptor complex and to other SAM molecules, and a terminal alkyne as a first cross-coupling moiety.

In step (2), receptor molecules (16) are incubated with a glycoprotein target molecule, which functions as a template (18). The receptor molecules (16) are acrylamide boronic acid monomers (AM-BA) comprising a boronic acid recognition moiety and an acrylamide polymerizable group, connected by an aryl linker. The BA recognition moiety binds to the glycosylation site of the glycoprotein template (18), forming a template-receptor complex (20).

In step (3), the template-receptor complex (20) is cross-linked to the SAM (10) via the acrylamide groups of the receptor molecules and the SAM molecules (14).

In step (4), a molecular scaffold is built around the template (18) using azide-terminated hepta(ethylene) (Az-OEG) scaffold molecules (22). The azide groups function as second cross-coupling moieties which react via click chemistry with the terminal alkynes of the SAM molecules, thereby immobilizing the scaffold molecules (22) on the SAM (10).

In step (5), the glycoprotein template (18) is removed by washing with water, leaving behind a cavity (24). The shape of the cavity (24) is complementary to and specific for the shape of the template (18), and thus provides a recognition or binding site that is selective for the target glycoprotein (18).

Figure 2:
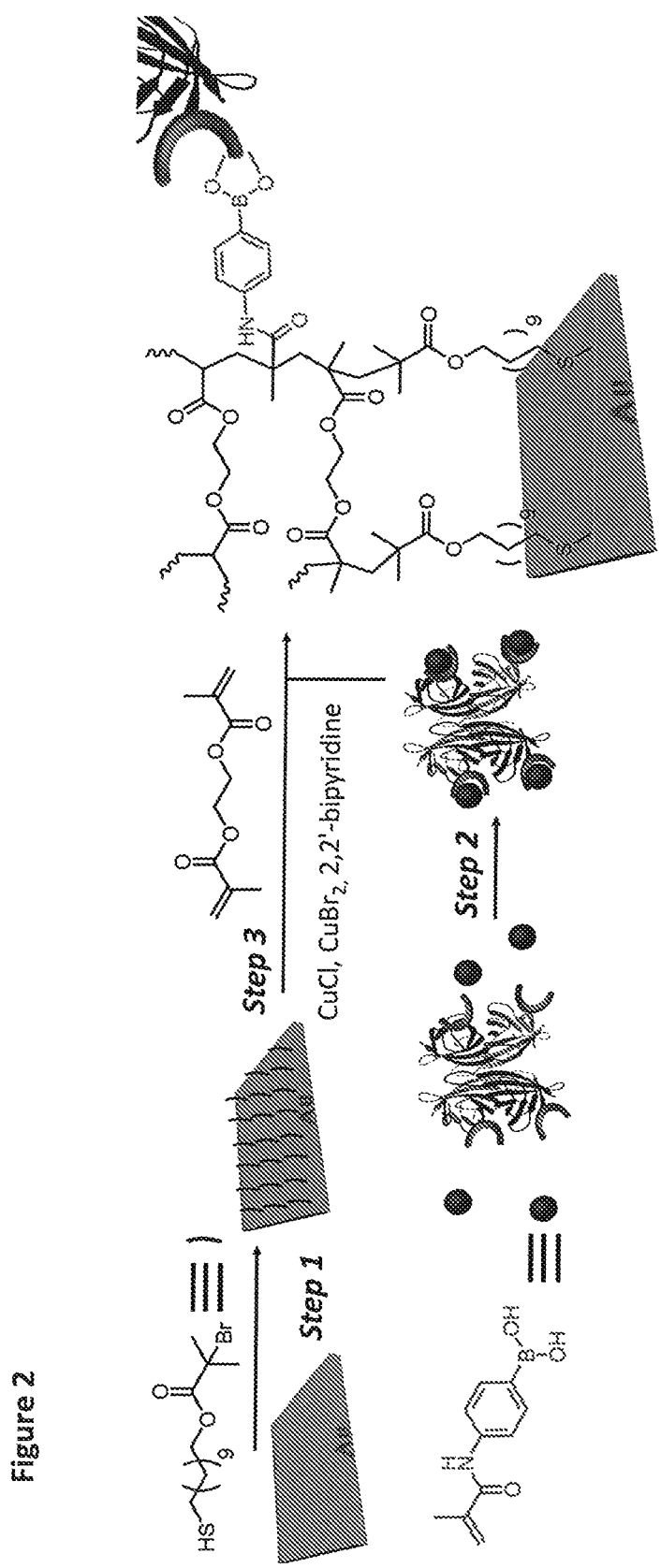
FIG. 2 is a schematic diagram showing the steps in the formation of a molecular sensor for a target protein according to an alternative embodiment of the present invention.

With reference to FIG. 2, a molecular sensor specific for a target molecule may alternatively be built using ATRP to produce an imprinted cross-linked film on a surface. In step (1), a SAM (30) is formed on a gold surface (32) using ATRP initiator-functionalized thiol molecules (34).

In step (2), receptor molecules (36) comprising a BA recognition motif and a vinyl polymerizable group are incubated with a target glycoprotein (38) in an aqueous medium to form a template-receptor complex (40).

In step (3), the SAM-functionalized gold surface (30, 32) is immersed in an aqueous solution containing EG dimethacrylate scaffold monomers (42), a catalyst (CuCl, $CuBr_2$, and/or 2,2'-bipyridine) and the template-receptor complex (40). The mixture is incubated for a period of time sufficient for polymerization to occur, resulting in a cross-linked film or scaffold (44) around the template.

In the final step (not shown), the template is removed by washing using a suitable solution, leaving behind an imprinted cross-linked film.

Figure 3:
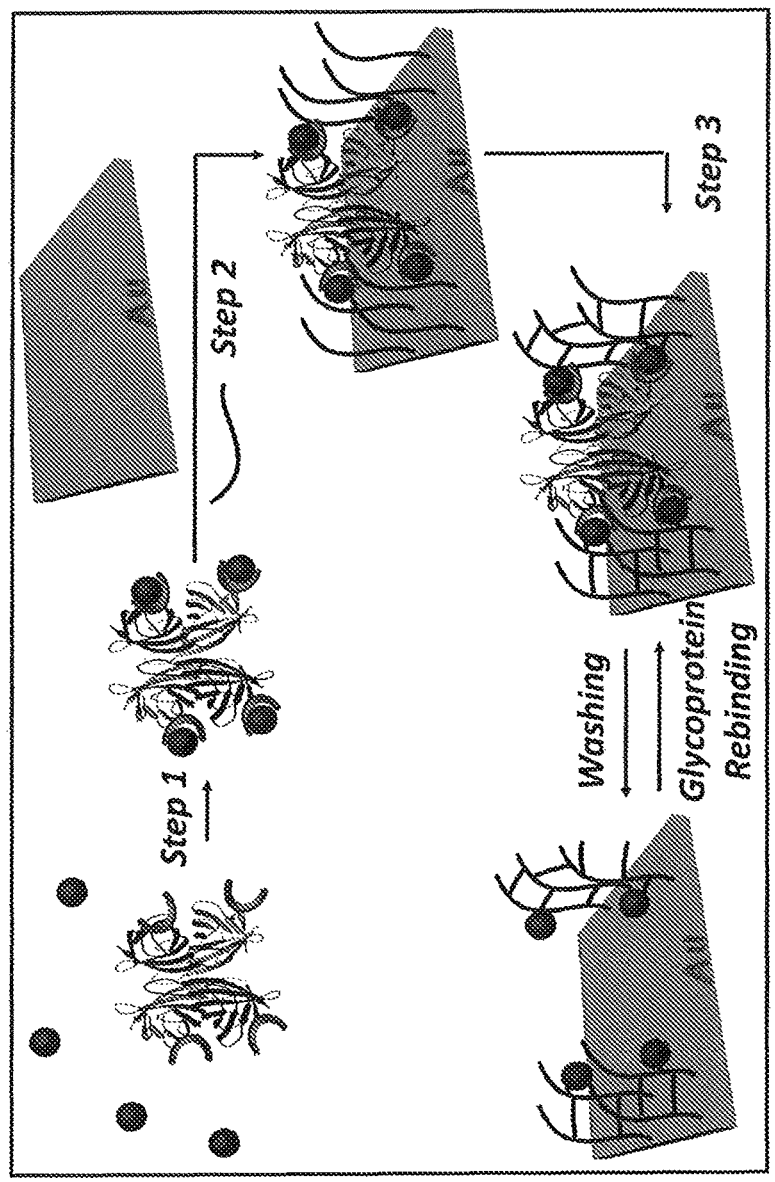
FIG. 3 is a schematic diagram showing the steps in the formation of a molecular sensor for a target protein according to a further embodiment of the present invention.

FIG. 3 shows a further method of preparing a molecular sensor specific for a target molecule. In step (1), receptor molecules (50) comprising a BA recognition motif and an acrylamide first binding moiety are incubated with a target glycoprotein (52) in an aqueous medium to form a template-receptor complex (54). Isothermal titration calorimetry (ITC) is used to determine the protein: receptor molar ratio required for saturation binding. It is preferred that no excess of receptors is used since unbound receptors could interfere with formation of the cavity and subsequent binding.

In step (2), the template-receptor complex (54) is simultaneously combined with a planar gold surface (56) and first molecules (58) comprising acrylamide binding moieties in an aqueous solution. By virtue of a tether moiety on the first molecules (58), the first molecules (58) and the template-receptor complex are adsorbed onto to the gold surface (56) to form a molecular scaffold (60).

In step (3), polymerization is initiated between the acrylamide binding moieties of the first molecules (58) and the receptor molecules (50), thereby forming a rigid network.

In step (4), the template is dissociated from the complex by washing, leaving behind a cavity (62) in the molecular scaffold (60) with receptors (50) at the surface thereof. The cavity (62) and the receptors (50) are thus available to bind target proteins in solution.

EXAMPLES

Methodology
Contact Angle

Contact angles were determined using a home-built contact angle apparatus, equipped with a charged coupled device (CCD) KP-M1E/K camera (Hitachi) that was attached to a personal computer for video capture. The dynamic contact angles were recorded as a micro-syringe was used to quasi-statically add liquid to or remove liquid from the drop. The drop was shown as a live video image on the PC screen and the acquisition rate was 4 frames per second. FTA Video Analysis software v1.96 (First Ten Angstroms) was used for the analysis of the contact angle of a droplet of UHP $H_2O$ at the three-phase intersection. The averages and standard errors of contact angles were determined from five different measurements made for each type of SAM.

Ellipsometry

The thickness of the deposited monolayers was determined by spectroscopic ellipsometry. A Jobin-Yvon UVISEL ellipsometer with a xenon light source was used for the measurements. The angle of incidence was fixed at 70°. A wavelength range of 280-820 nm was used. The DeltaPsi software was employed to determine the thickness values and the calculations were based on a three-phase ambient/SAM/Au model, in which the SAM was assumed to be isotropic and assigned a refractive index of 1.50. The thickness reported is the average and standard error of six measurements taken on each SAM.

X-Ray Photoelectron Spectroscopy (XPS)

Elemental composition of the SAMs were analysed using an Escalab 250 system (Thermo VG Scientific) operating with Avantage v1.85 software under a pressure of $\sim 5 \times 10^{-9}$ mbar. An Al Kα X-ray source was used, which provided a monochromatic X-ray beam with incident energy of 1486.68 eV. A circular spot size of $\sim 0.2$ $mm^2$ was employed. The samples were attached onto a stainless steel holder using double-sided carbon sticky tape (Shintron tape). In order to minimise charge retention on the sample, the samples were clipped onto the holder using stainless steel or Cu clips. The clips provided a link between the sample and the sample holder for electrons to flow, which the glass substrate inhibits. Low resolution survey spectra were obtained using a pass energy of 150 eV over a binding energy range of 0 eV to 1250 eV obtained using 1 eV increments. The spectra recorded were an average of 3 scans. The high resolution spectra were obtained using a pass energy of 20 eV and 0.1 eV increments over a binding energy range of 20-30 eV, centred on the binding energy of the electron environment being studied. A dwell time of 50 ms was employed between each binding energy increment. The spectra recorded were an average of between 5-250 scans (N (1s)=100, Au (4f)=5, S (2p)=150, B (1s)=250, 0 (1s)=50, C (1s)=50). Sensitivity factors used in this study were: N (1s), 1.8; Au (4f), 17.1; S (2p), 1.68; B (1s), 0.486; 0 (1s), 2.93; C (1s), 1.0.

Surface Plasmon Resonance (SPR)

SPR experiments were performed with a Reichert SR7000DC Dual Channel Spectrometer (Buffalo, N.Y., USA) at 25° C. Prior to the binding studies, a baseline for the SAMs was established by running degassed PBS pH 8.5 through the machine at a flow rate of 25 µl/min.

Example 1: SAM Preparation

Polycrystalline gold substrates were purchased from George Albert PVD., Germany and consisted of a 50 nm gold layer deposited onto a glass covered with a thin layer of chromium. The Au substrates were cleaned by immersion in piranha solution (7:3, $H_2SO_4$:$H_2O_2$) at room temperature for 10 min. Samples removed from the piranha solution were immediately rinsed with Ultra High Pure (UHP) $H_2O$, followed by HPLC grade methanol (Fischer Scientific) for 1 min. Immediately after cleaning, the substrates were immersed in freshly prepared 0.1 mM methanolic solutions of AAM-SS molecules for 18 hours. Post-immersion in the SAM forming solution, the substrates were rinsed with HPLC MeOH and dried with a stream of argon.

The AAM-SS SAMs were characterized by ellipsometry and contact angle, exhibiting a thickness and wetting properties consistent with the formation of a stable, sparsely packed monolayer (Table 1). The presence of AAM-SS SAMs was further confirmed by X-ray photoelectron spectroscopy, producing the expected surface elemental ratios (Table 1).

In order to confirm that the alkyne and acrylic groups on the AAM-SS SAM are accessible and able to participate in surface reactions with AM-BA via acrylic polymerisation or Az-OEG via click chemistry, respectively, the AAM-SS SAMs were independently modified with AM-BA or Az-OEG.

Crosslinking of AAM-SS SAMs with AM-BA was initiated using ammonium persulphate. SAMs of AAM-SS were placed in 1 ml 1 mM of AM-BA monomers in UHQ $H_2O$, to which 100 µl of ammonium persulphate was added (40 mg/ml). The resulting mixture was then allowed to react for 15 minutes. After this time, the chips were removed from the crosslinking solution and rinsed for one minute with UHQ $H_2O$. Samples were then dried under a stream of argon before being characterized by contract angle, ellipsometry and XPS.

Click reactions were carried out between AAM-SS SAMs and Az-OEG. 1.2 ml of a 5 mM solution of Az-OEG was mixed with 150 µl of both copper sulphate (40 mM) and sodium ascorbate (100 mM). AAM-SS SAMs were placed in click reaction solutions and allowed to react for between 0.5 to 24 hours. After reaction chips were removed from the click solution and rinsed well with UHQ water and sonicated with 0.1 mM EDTA solution to remove any copper, prior to surface characterization. Again all surfaces were characterised by contact angle, ellipsometry and XPS.

Preparation of BA-AAM-SS monolayers by crosslinking at room temperature AAM-SS SAM with AM-BA led to a decrease in wettability and, as expected, to an increase in thickness of the film (Table 1).

TABLE 1

Ellipsometric thickness, advancing and receding contact angles and nitrogen/sulphur (N/S) XPS ratio of the different monolayers investigated.

| SAM | Thickness (nm) | | Contact angle (°) | | N/S XPS ratio | |
|---|---|---|---|---|---|---|
| | Observed | Theoretical | Advancing | Receding | Observed | Expected |
| AAM-SS | 0.42 ± 0.2 | 0.91 | 65.1 ± 1.15 | 46.94 ± 3.84 | 1.9 | 2 |
| BA-AAM-SS | 0.82 ± 0.3 | 0.85 | 44.9 ± 5.4 | 39.4 ± 7.7 | 2.95 | 3 |
| OEG-AAM-SS | 1.95 ± 0.12 | 2.9 | 39.9 ± 3.5 | 31.3 ± 3.2 | 5.38 | 5 |

Example 2: Sensor Fabrication

To form the sensor, a one pot multi-step template procedure was used. A solution of AM-BA was mixed with a 10 fold excess of the target protein, all adjusted to pH 8.5. This was allowed to incubate for 30 minutes, after which the SAMs were placed in the resultant solution. To this 100 µl of ammonium persulfate solution (40 mg/ml) was added to initiate cross-linking. The solution was then incubated for a further 5 minutes. To this solution 1 ml of a 5 mM solution of O-(2-Azidoethyl)heptaethylene glycol was added. After 10 minutes the click reaction was initiated by the addition of a 30 µl solution of pre-prepared catalyst (15 µl of 40 mM Copper sulphate and 15 µl of 100 mM sodium ascorbate). The mixture was then allowed to react for a total for 4 hours. After the reaction time had been reached the SPR chips were removed from the reaction solution and rinsed with liberal amount of UHQ $H_2O$ for 3 minutes to remove bound template protein.

Following rinsing of the template compounds from the cavities, SPR binding experiments were used to confirm the selectivity of molecularly imprinted sensors. All SPR experiments were conducted at 25° C., with a SPR flow rate of 25 µl/min, using a 150 µl loop. Stock protein solutions were prepared from freeze dried proteins, using an accurate balance to produce a final concentration of 1 mg/ml. For SPR experiments, protein samples were prepared by a 1:10 dilution of the stock solution, followed by a serial dilution to produce samples of 100, 50, 25 and 12.5 µl of each protein. Molar concentrations of each protein were then calculated from published mass data. Protein samples were injected for a 5 minute association phase before switching back to buffer for the dissociation phase for up to 10 minutes. The same injection protocol was used to regenerate the surface in between sample injections, using an acidic regeneration solution.

It was found that the surfaces displayed a much higher equilibrium binding response to target proteins than to non-target proteins (see below). This is indicative of the nano-cavities adopting a surface conformation which offers a complementary binding site to the target protein, which results in an increased affinity.

Example 3: PSA Sensor

A sensor for the detection of PSA was fabricated using the method described in Example 2. Once formed, the ability of the sensor to bind proteins was investigated using SPR and from the SPR data dissociation constants ($K_d$) were calculated.

The PSA-imprinted surface exhibited excellent selectivity towards PSA, with all other proteins showing significantly reduced affinity (Table 2). A dissociation constant of 1.8 µM is comparable to the value for other antibodies specific for PSA (typically with values in the nM-µM range).

TABLE 2

Affinity data for PSA (target molecule) and other proteins

| Protein | $K_d$ (µM) |
|---|---|
| PSA | 1.8 ± 0.1 |
| Lysozyme | 4.9 ± 0.1 |
| α-1-acid glycoprotein (α1-AGP) | 5.3 ± 0.1 |
| RNAse B | 6.7 ± 0.5 |
| Bovine serum albumin (BSA) | 21.6 ± 0.6 |
| α-1-antitrypsin α1-AT | 30.9 ± 0.9 |
| horseradish peroxidase (HRP) | 52.5 ± 2.0 |

The PSA-imprinted surface revealed a 3-30 fold selectivity to PSA over other glycosylated and non-glycosylated proteins. The difference in the magnitude of the binding affinity between the non-targeted proteins appears to be primarily attributed to their molecular size (Table 3), in which proteins of similar or smaller size to that of the target PSA displayed higher binding affinities than other larger proteins examined. There is no observable general trend in the amount of non-target protein bound to the imprinted surface with isoelectric point. It is noted however that positively charged proteins at pH 8.5 are more prone to interact with the negatively charged boronate ion species present in the imprinted surfaces. Thus, it is reasonable to explain the higher affinity of lysozyme among the non-target proteins for the PSA-imprinted surfaces based on Coulombic interactions.

Although it could have been hypothesised that a higher degree of glycosylation would induce a higher non-specific binding from the non-targeted glycoproteins due to the interaction of the sugar residues with the BA containing-nanocavities, such trend is not established by the data. Remarkably, ribonuclease (RNAse) B, which is a smaller glycoprotein than PSA with similar degree of glycosylation, produced a very low SPR response when evaluated at concentrations as high as 650 nM.

template proteins. Dissociation constants calculated from the SPR data for RNase B and various non-target proteins are given in Table 4 below. These data demonstrate that the molecularly imprinted surface was able to distinguish between the target protein and non-target proteins with a high degree of selectivity (10-200 fold selectivity to RNase B over other glycosylated and non-glycosylated proteins).

TABLE 3

| Protein | PSA | Lysozyme | α1-AGP | RNAse B | BSA | α1-AT | HRP |
|---|---|---|---|---|---|---|---|
| size (nm × nm × nm) | 4.4 × 4.1 × 5.1[a] | 2.8 × 3.2 × 3[b] | 5.9 × 4.2 × 3.9[a] | 3.8 × 2.8 × 2.2[b] | 14 × 4 × 4[b] | 7 × 3 × 3[b] | 4.0 × 6.7 × 11.7[b] |
| glycosylation (%) | 8.3 | 0 | 45 | 9 | 0 | 5 | 21 |
| Isoelectric point | 6.2-7.5 | 11.1 | 2.8-3.8 | 9.2-9.6 | 4.7 | 4.5-5.5 | 9 |

[a] estimated using ChemBio Ultra 3D
[b] literature values

It is important to note that OEG-terminated surfaces created without the glycoprotein-AM-BA complex displayed minimal non-specific protein binding, with SPR responses below 20 response units. The low binding of RNAse B to the PSA-imprinted surface provides evidence that spatially arranged sets of BAs on the surface that are specific for the target PSA glycoprotein have been created. Furthermore, SPR analysis revealed the detection of PSA at nM levels and excellent reproducibility of the imprinted surfaces. The surface coverage for PSA was found to range between 0.024 ng/mm² and 0.140 ng/mm² (100 response units (RUs) 0.1 ng/mm), depending on the concentration of PSA to which the sensor was exposed to. By converting surface coverage mass into molecular units of PSA (Mw=28.4 kDa) per mm², 81 nM has led to a coverage of $5.1 \times 10^8$ PSA molecules/mm² whereas a 8 fold increase in concentration (i.e. 650 nM) raised the coverage to $3.0 \times 10^9$ PSA molecules/mm². This value is below the maximum amount of PSA that can be captured on the imprinted surface as determined by $T_{max}$ (Equation 1) and identified to occur at $9.8 \times 10^9$ PSA molecules/mm². Taking dimensions of PSA to be 4.4 nm×4.1 nm×5.1 nm (Table 3), and assuming ellipsoidal projection onto a plane, the ideal PSA surface coverage is approximated to be $1.4 \times 10^{10}$ PSA molecules/mm². These results established that the imprinted surfaces can attain high surface coverage (70%) by PSA, with the remaining OEG non-nanocavity areas on the surface providing the desired interprotein distance for efficient binding affinity and selectivity.

$$R_{eq} = \left( \frac{C_p}{C_p + K_D} \right) R_{max} \quad \text{Equation 1}$$

where
$R_{eq}$ is the SPR response at equilibrium
$C_p$ is the concentration of injected protein
$K_d$ is the dissociation constant for binding of the protein to the survace
$R_{max}$ is the maximum response if all available binding sites are occupied Example 4: RNAse B Sensor A sensor for the detection of RNAse B was fabricated using the method described in Example 2. Once formed, the ability of the sensor to bind proteins was investigated using SPR. It was observed that the response to RNase B (the template protein) was significantly higher than that to non- Although RNAse B and lysozyme have not so dissimilar dimensions and isoelectric points (Table 3), the RNAse B-imprinted surface revealed a 8-fold enhanced selectivity for RNAse B over lysozyme, supporting the notion that BA carbohydrate receptors on the glycoprotein-imprinted surfaces contribute to the selectivity and affinity of the imprinted surface.

TABLE 4

Affinity data for RNase B (target molecule) and other proteins

| Protein | $K_d$ (μM) |
|---|---|
| RNase B | 3.1 ± 0.1 |
| Lysozyme | 24.3 ± 0.1 |
| BSA | 33.8 ± 0.6 |
| HRP | 119 ± 2 |
| α1-AGP | 201 ± 7 |
| α1-AT | 570 ± 50 |

One goal of this work was to develop a system which is able not only to distinguish between different proteins, but to be able to distinguish between different forms of the same protein, specifically the saccharide on the surfaces. To this end the fabrication process was repeated to create more RNase selective surfaces. Solutions of RNase A and RNase B were injected onto these surfaces, and the binding responses were monitored. It was observed that the RNase B solutions produced a higher response at the same concentrations than the RNase A. Furthermore, kinetic analysis demonstrated that the surfaces were able to demonstrate a higher affinity for the RNase B (Table 5), indicating that the stronger interactions are dictated by the presence of the glycan on RNase B, and in turn its specific covalent bond formation with the spatially immobilised BA moieties on the surface. The weaker RNAse A interactions are considered to have arisen to some extent from Coulombic interactions between the known positively charged RNAse A domain along its longest axis and the negatively charged boronate ion species present in the imprinted surfaces.

TABLE 5

Affinity data for binding of RNAse A and RNAse B to a molecular sensor produced using RNAse B as the template.

| Protein | $K_d$ |
|---|---|
| RNAse B | 3.1 ± 0.1 μM |
| RNaseA | 8.0 ± 0.1 μM |

Bare RNAse B-imprinted surfaces (absence of BA molecules in the nanocavities) exhibited lower affinity and rather poor specificity, capturing the glycoprotein template and its non-glycosylated form in a similar fashion. The bare RNAse B-imprinted surfaces resulted in about 7-fold reduced affinity to RNAse B compared with the BA-containing RNAse B-imprinted surface. These observations further highlight that the overall binding strength and selectivity of the imprinted surface towards the target glycoprotein arises from two distinct effects: shape matching and specific covalent interactions between the active tetrahedral boronate ion and the sugar residues in the glycoprotein.

Sensitivity of the imprinted surfaces for the target glycoprotein in complex biological conditions such as serum was also investigated. Simultaneous adsorption of RNAse B (ranging from 0.01 mg/ml to 0.1 mg/ml) and 0.5% serum (i.e. 0.32 mg/ml) on RNAse B-imprinted surfaces was monitored by SPR. In order to eliminate the background signal, the RNAse-B imprinted surfaces were initially blocked with 0.5% serum, thereby allowing it to bind to all potential sites of non-specific interaction. The blocked RNAse-B imprinted surfaces were shown to provide highly sensitive detection for RNAse B at levels as low as 3% (w/w). The slightly reduced affinity of RNAse B towards the blocked RNAse-B imprinted surfaces ($K_d$=6.5 µM±0.2) in comparison with bare RNAse-B imprinted surfaces ($K_d$=3.1 µM±0.1) can be explained as a result of the blocking and elimination of the non-specific contribution to the overall binding affinity of RNAse B to the imprinted surface and/or serum competition for binding sites.

Reusing a functionalised sensing surface is a highly desirable feature. For this reason, the performance of the RNAse B-imprinted surface in the serial capture and acidic regeneration of RNAse B was evaluated. The cycles were recorded by repeatedly injecting 0.85 µM solutions of RNAse B for 5 min, followed by PBS buffer for 10 min, regeneration with an acidic solution for 5 min and PBS buffer for 10 min. As illustrated in FIG. 4, the imprinted surfaces were shown to be remarkably stable for more than 10 cycles of binding and regeneration of the surface.

Example 5: Maltose Sensor

A sensor for the detection of maltose was fabricated using the method described in Example 2 (save for the omission of the O-(2-Azidoethyl)heptaethylene glycol addition) with maltose as the template. FIG. 6 (panel A) shows SPR plots at varying concentrations for 3 disaccharides (palatinose, maltose and cellobiose) for a standard boronic acid terminated surface (i.e. not in accordance with the invention) and panel B shows SPR plots for the maltose sensor. Boronic acid preferentially binds fructose, hence the stronger affinity shown for palatinose (glucose-fructose, as opposed to cellobiose and maltose which have differently configured glucose-glucose structures) with the unimprinted surface (Panel A). When a maltose template is used and the boronic acids are fixed, the surface binds more strongly to maltose (Panel B). This result demonstrates that selectivity for a particular oligosaccharide can be created using the methods of the invention.

The invention claimed is:

1. A method of preparing a molecular sensor that is specific for a target molecule having a saccharide or peptide region, the method comprising, in a stepwise manner:

using the target molecule as a template, mixing a solution of receptor molecules capable of selectively and reversibly binding the target molecule with a solution of the target molecule and incubating the template with the receptor molecules to form a template-receptor complex, wherein the target and the receptor molecules in the solution are provided in a molar ratio for saturation binding so as to avoid an excess of the receptor molecules in the solution and enable substantially all of the receptor molecules to bind to a target molecule in the solution;

forming a molecular scaffold on a surface around the template-receptor complex such that the receptor and at least a portion of the template are embedded in the scaffold; and removing the template from the template-receptor complex of the molecular scaffold to produce a cavity defined by the molecular scaffold, wherein:

the cavity is complementary to at least a portion of the saccharide or peptide region of the target molecule and comprises one or more receptor molecules at a surface thereof, the spatial arrangement of the one or more receptor molecules being specific for saturation binding of the target molecule.

2. The method of claim 1, wherein the step of removing the template comprises dissociating the template from the receptor, thereby producing a cavity having the receptor molecules at the surface thereof.

3. The method of claim 1, wherein the receptor molecules comprise a recognition motif which is capable of selectively and reversibly binding the target molecule.

4. The method of claim 3, wherein the target molecule is a glycoprotein and the recognition motif binds to the saccharide or the peptide region of the glycoprotein.

5. The method of claim 3, wherein the recognition motif comprises a boronic acid group.

6. The method of claim 1, wherein the receptor molecules comprise a first binding moiety for binding the template-receptor complex to the molecular scaffold, and wherein the first binding moiety is a polymerizable group.

7. The method of claim 1, wherein the molecular scaffold is formed from a first type of molecules, each of the first type of molecules comprising a tether moiety for tethering the molecular scaffold to the surface, and wherein the tether moiety is a thiol, a disulfide, an organosilane, a dialkyl sulfide, an alcohol, an amine or a carboxylic acid group.

8. The method of claim 7, wherein the step of forming the molecular scaffold comprises exposing the surface to the first type of molecules so as to allow adsorption of the first type of molecules onto the surface and wherein the first type of molecules form a self-assembled monolayer (SAM) on the surface.

9. The method of claim 8, wherein the surface is exposed to the first type of molecules in the presence of the template-receptor complex.

10. The method of claim 8, further comprising cross-linking the first type of molecules after adsorption of the molecules onto the surface.

11. The method of claim 8, wherein each of the first type of molecules comprises a second binding moiety capable of binding to other of the first type of molecules, to the receptor and/or to further molecules, and wherein the second binding moiety is a polymerizable group.

12. The method of claim 1, wherein the molecular scaffold is formed from a first type of molecules and a second type of molecules.

13. The method of claim 12, wherein at least one of the first and second types of molecules comprises an elongate moiety comprising ethylene glycol, or an oligomer thereof.

14. The method of claim 12, comprising:
forming a SAM on a surface from a first type of molecules;
using the target molecule as a template, mixing a solution of the receptor molecules capable of selectively and reversibly binding the target molecule with the solution of the target molecule and incubating the template with the receptor molecules to form the template-receptor complex, wherein the target and the receptor molecules in the solution are provided in a molar ratio for saturation binding so as to avoid an excess of the receptor molecules in the solution and enable substantially all of the receptor molecules to bind to a target molecule in the solution, and binding the template-receptor complex to the SAM;
immobilizing a second type of molecules on the SAM so as to form a molecular scaffold around the bound template; and
removing the template from the template-receptor complex of the molecular scaffold to produce a cavity defined by the molecular scaffold, wherein the cavity is complementary to at least a portion of the saccharide or peptide region of the target molecule.

15. The method of claim 14, wherein each of the first type of molecules comprises a first coupling moiety for coupling to the second type of molecules, wherein each of the second type of molecules comprises a second coupling moiety for coupling to the first type of molecules, to other of the second type of molecules and/or to the receptors, and wherein the second type of molecules are immobilized on the SAM by a reaction between the first coupling moieties of the first type of molecules and the second coupling moieties of the second type of molecules.

16. The method of claim 15, wherein the second type of molecules are immobilized on the SAM by a click reaction between the first coupling moieties of the first type of molecules and the second coupling moieties of the second type of molecules.

17. The method of claim 12, comprising:
forming a SAM on a surface using the first type of molecules;
using the target molecule as the template, mixing the solution of the receptor molecules capable of selectively and reversibly binding the target molecule with the solution of the target molecule and incubating the template with the receptor molecules to form the template-receptor complex, wherein the target and the receptor molecules in the solution are provided in a molar ratio for saturation binding so as to avoid an excess of the receptor molecules in the solution and enable substantially all of the receptor molecules to bind to a target molecule in the solution;
exposing the SAM-functionalized surface to a mixture of the second type of molecules, the template-receptor complex and a catalyst so as to effect atom transfer radical polymerization (ATRP) between the first molecules, the second molecules and the receptor, thereby forming a molecular scaffold around the template; and
removing the bound template from the template-receptor complex of the molecular scaffold to produce a cavity defined by the molecular scaffold, wherein the cavity is complementary to at least a portion of the saccharide or peptide region of the target molecule.

18. The method of claim 17, wherein each of the first type of molecules comprises an ATRP initiator and wherein each of the second type of molecules comprises at least one second cross-coupling moiety which is a polymerizable group.

19. The method of claim 1, comprising:
using the target molecule as a template, mixing the solution of the receptor molecules capable of selectively and reversibly binding the target molecule with the solution of the target molecule and incubating the template with the receptor molecules to form the template-receptor complex, wherein the target and the receptor molecules in the solution are provided in a molar ratio for saturation binding so as to avoid an excess of the receptor molecules in the solution and enable substantially all of the receptor molecules to bind to a target molecule in the solution, wherein the receptor comprises a polymerizable group;
exposing a surface to a first type of molecules in the presence of the template-receptor complex, each of the first type of molecules comprising a tether moiety and a polymerizable group;
initiating polymerization between the polymerizable groups so as to form a molecular scaffold on the surface around the template-receptor complex, wherein the receptor is covalently bound to the scaffold and at least a portion of the template is embedded in the scaffold; and
removing the template from the template-receptor complex of the molecular scaffold to produce a cavity defined by the molecular scaffold, wherein the cavity is complementary to at least a portion of the saccharide or peptide region of the target molecule.

20. The method of claim 1, wherein the surface is a surface of a nanoparticle.

21. A method of preparing a molecular sensor that is specific for a target molecule having a saccharide or peptide region, the method comprising, in a stepwise manner:
using the target molecule as a template, mixing a solution of receptor molecules capable of selectively and reversibly binding the target molecule with a solution of the target molecule and incubating the template with the receptor molecules to form a template-receptor complex, wherein the target and the receptor molecules in the solution are provided in a molar ratio for saturation binding, so as to avoid an excess of the receptor molecules in the solution and enable substantially all of the receptor molecules to bind to a target molecule in the solution;
forming a molecular scaffold on a surface around the template-receptor complex such that the receptor and at least a portion of the template are embedded in the scaffold; and
removing the template from the template-receptor complex of the molecular scaffold to produce a cavity defined by the molecular scaffold, wherein:
the cavity is complementary to at least a portion of the saccharide or peptide region of the target molecule and comprises spatially arranged sets of the receptor molecules on the surface that are specific for the target molecules, and
the molecular scaffold is formed from a first type of molecules, each of the first type of molecules comprising a tether moiety for tethering the molecular scaffold to the surface.

* * * * *